United States Patent
Takasu (10) Patent No.: US 8,536,873 B2
(45) Date of Patent: Sep. 17, 2013

(54) SUBSTANCE DETECTION METHOD AND SUBSTANCE DETECTION DEVICE

(75) Inventor: Ryozo Takasu, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 307 days.

(21) Appl. No.: 13/050,731

(22) Filed: Mar. 17, 2011

(65) Prior Publication Data

US 2011/0234234 A1  Sep. 29, 2011

(30) Foreign Application Priority Data

Mar. 26, 2010  (JP) .................................. 2010-72119

(51) Int. Cl.
*G01N 27/62* (2006.01)
(52) U.S. Cl.
USPC ......................................................... 324/464
(58) Field of Classification Search
None
See application file for complete search history.

(56) References Cited

U.S. PATENT DOCUMENTS

2010/0009469 A1* 1/2010 Kai et al. .......................... 438/7

FOREIGN PATENT DOCUMENTS

JP   2002-48797   2/2002
JP   2009-098084   5/2009

* cited by examiner

*Primary Examiner* — Melissa Koval
*Assistant Examiner* — Trung Nguyen
(74) *Attorney, Agent, or Firm* — Fujitsu Patent Center (57) ABSTRACT

A detection method of detecting a target substance, the method includes exciting the target substance by irradiating an atmosphere of a detection space with light having a first wavelength that excites the target substance from a ground state to an excited state on the basis of the energy level structure of the target substance; ionizing the target substance by irradiating the atmosphere of the detection space with light having a second wavelength that excites the target substance from the excited state to an energy state substantially equal to or higher than a vacuum level; making the ionized target substance adsorb to a detector by electric field acceleration; and detecting the amount of adsorption of the target substance.

9 Claims, 6 Drawing Sheets

| MOLECULE | IONIZATION ENERGY [eV] |
|---|---|
| NAPHTHALENE | 8.14 |
| 1,3,5-TRIMETHYLBENZENE | 8.4 |
| STYRENE | 8.46 |
| M-XYLENE | 8.55 |
| ETHYLBENZENE | 8.77 |
| TOLUENE | 8.83 |
| BENZENE | 9.245 |
| NITROBENZENE | 9.94 |
| AMMONIA | 10.154 |
| HYDROGEN SULFIDE | 10.46 |
| METHANOL | 10.85 |
| FORMALDEHYDE | 10.87 |
| METHYL CHLORIDE | 11.18 |
| OXYGEN | 12.075 |
| SULFUR DIOXIDE | 12.44 |
| WATER | 12.61 |
| NITROGEN DIOXIDE | 13.88 |
| NITROGEN | 15.577 |

FIG. 5

SUBSTANCE DETECTION METHOD AND SUBSTANCE DETECTION DEVICE

CROSS-REFERENCE TO RELATED APPLICATIONS

This application is based upon and claims the benefit of priority of the prior Japanese Patent Application No. 2010-072119, filed on Mar. 26, 2010, the entire contents of which are incorporated herein by reference.

FIELD

The present invention relates to a substance detection method and a substance detection device.

BACKGROUND

In the field of manufacturing electronic devices, for example, semiconductor devices, organic substances and the like contained in the atmosphere of the manufacturing environment, for example, clean rooms, affect device performance and fabrication yield. These organic substances and the like are referred to herein as target substances. Consequently, it is desired to detect these target substances in the atmosphere.

In order to detect, by a simple method, target substances in the atmosphere, quartz crystal microbalance (QCM) sensors and the like using a quartz oscillator are used. QCM sensors utilize a phenomenon that the oscillation frequency of the quartz oscillator varies with a change in weight of the oscillator. In QCM sensors, when substances in the atmosphere adsorb to the surface of the oscillator, the presence of the substances is detected by a change in oscillation frequency of the quartz oscillator.

QCM sensors are used for environmental control in manufacturing plants and atmospheric control at various places. As substance sensors, in addition to QCM sensors using a quartz oscillator, sensors using a surface acoustic wave (SAW) element are also known.

For example, Japanese Unexamined Patent Application Publication No. 2002-48797 discloses a monitoring device and a monitoring method therefor in which an antibody that will bond to a specific substance to be measured is attached to the surface of an oscillator, and by measuring the change in output frequency of the oscillator with time, the change in mass of the substance bonded to the antibody is detected.

In the case where a quartz oscillator, which is used as a piezoelectric element, is provided with an antibody that is to be specifically bonded to a chemical substance (antigen) to be measured, and is oscillated by an oscillation circuit, the quartz oscillator oscillates with a given frequency in proportion to the amount of adsorption (mass) of the antibody. In this case, if the antibody reacts with the antigen, the mass of the quartz oscillator changes because of the reaction product. The change in mass is related to the change in frequency (number of oscillations) of the quartz oscillator in accordance with the equation: $\Delta f = k f_0^2 (\Delta w/A)$, where $f_0$ is the initial frequency of the quartz oscillator, $\Delta f$ is the change in frequency, $\Delta w$ is the change in mass, A is the area of antigen deposited on the quartz oscillator, and k is the constant. For example, when a quartz oscillator with an initial frequency of 9 MHz is used, a change in mass of the conductive thin film of 0.5 ng/cm2 due to an antigen-antibody reaction can be measured with a sensitivity of 1 Hz.

For example, Japanese Unexamined Patent Application Publication No. 2009-98084 discloses an atmosphere analyzer which includes a counter electrode disposed so as to face a sensor electrode, in which a voltage is applied between the sensor electrode and the counter electrode to accelerate ions, and which includes an ultraviolet light source for applying ultraviolet light to the space between the sensor electrode and the counter electrode. When a target substance in the space is ionized by ultraviolet light, ions are driven by the electric field and adsorb to the sensor electrode. When irradiation with ultraviolet light is stopped, generation of ions is stopped. The sensitivity to the target substance can be improved by extracting the difference in signal between during irradiation with ultraviolet light and during non-irradiation with ultraviolet light.

SUMMARY

According to an aspect of the invention, a detection method of detecting a target substance, the method includes exciting the target substance by irradiating an atmosphere of a detection space with light having a first wavelength that excites the target substance from a ground state to an excited state on the basis of the energy level structure of the target substance; ionizing the target substance by irradiating the atmosphere of the detection space with light having a second wavelength that excites the target substance from the excited state to an energy state substantially equal to or higher than a vacuum level; making the ionized target substance adsorb to a detector by electric field acceleration; and detecting the amount of adsorption of the target substance.

According to another aspect of the invention, a detection device includes a detector configured to detect the amount of adsorption of a target substance; a counter electrode configured to face the detector with a detection space therebetween; a first light source configured to irradiate the detection space with light having a first wavelength having an energy substantially equal to a difference between a ground energy level and an excited energy level of the target substance; a second light source configured to irradiate the detection space with light having a second wavelength having an energy substantially equal to or higher than a difference between the excited energy level and a vacuum level of the target substance; an acceleration power source configured to form an acceleration electric field between the counter electrode and the detector; and a detection circuit configured to supply a detection signal to the detector.

The object and advantages of the invention will be realized and attained by at least those elements, features, and combinations particularly pointed out in the claims.

It is to be understood that both the foregoing general description and the following detailed description are exemplary and explanatory and are not restrictive of the invention, as claimed.

DESCRIPTION OF EMBODIMENTS

Figure 4A:
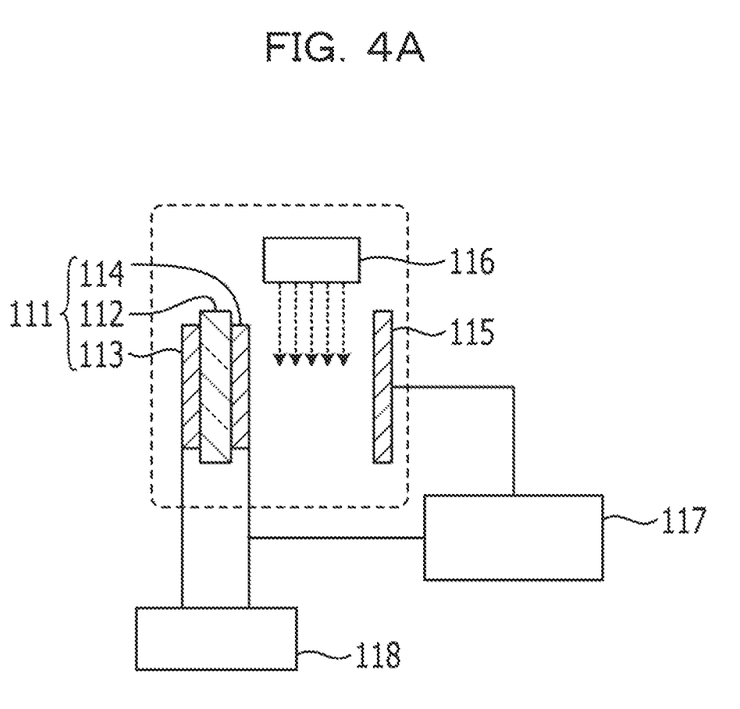
FIG. 4A is a block diagram of an atmosphere analyzer.

FIG. 4A is a block diagram illustrating a portion of an atmosphere analyzer. A quartz oscillator 111, which includes a quartz plate 112 and electrodes 113 and 114 provided on surfaces thereof, is exposed to an atmosphere containing a pollutant which is a detection target (i.e., target substance). A counter electrode 115 is disposed at a distance from the electrode 113. An ultraviolet light source 116 applies ultraviolet light to the space between the electrode 113 and the counter electrode 115. An oscillation circuit 118 is coupled between the electrodes 113 and 114, and a DC voltage source 117 is coupled between the electrode 113 and the counter electrode 115. The distance between the electrode 113 and the counter electrode 115 is, for example, 3 mm to 10 mm. The voltage of the DC voltage source 117 is, for example, a voltage that produces an electric field of 100 V/cm or more between the electrode 113 and the counter electrode 115.

The ultraviolet light source 116 is a deuterium discharge tube with a MgF2 window, which emits, for example, ultraviolet light with an energy of 10.78 eV or less. Many organic substances have an ionization energy which belongs to the vacuum ultraviolet region and which is 10.78 eV or less, and thus can be ionized by ultraviolet light. The required intensity of ultraviolet light is, for example, about 5×10-8 W/cm2 or more.

The DC voltage source 117 forms an acceleration electric field between the electrode 113 and the counter electrode 115. When ions are generated by ultraviolet light, the ions are accelerated by the acceleration electric field toward the electrode 113 and adsorb to the electrode 113. The quartz oscillator 111 is oscillated by application of a voltage to the pair of electrodes 113 and 114 from the oscillation circuit 118. When the mass of the oscillator increases because of the adsorbed ions, the oscillation frequency changes. The mass of the adsorbed substance can be detected on the basis of the change in frequency. By controlling the on/off of irradiation of ultraviolet light, ionization can be performed by ultraviolet light, and the substance adsorbed to the oscillator can be detected with high sensitivity.

Figure 4B:
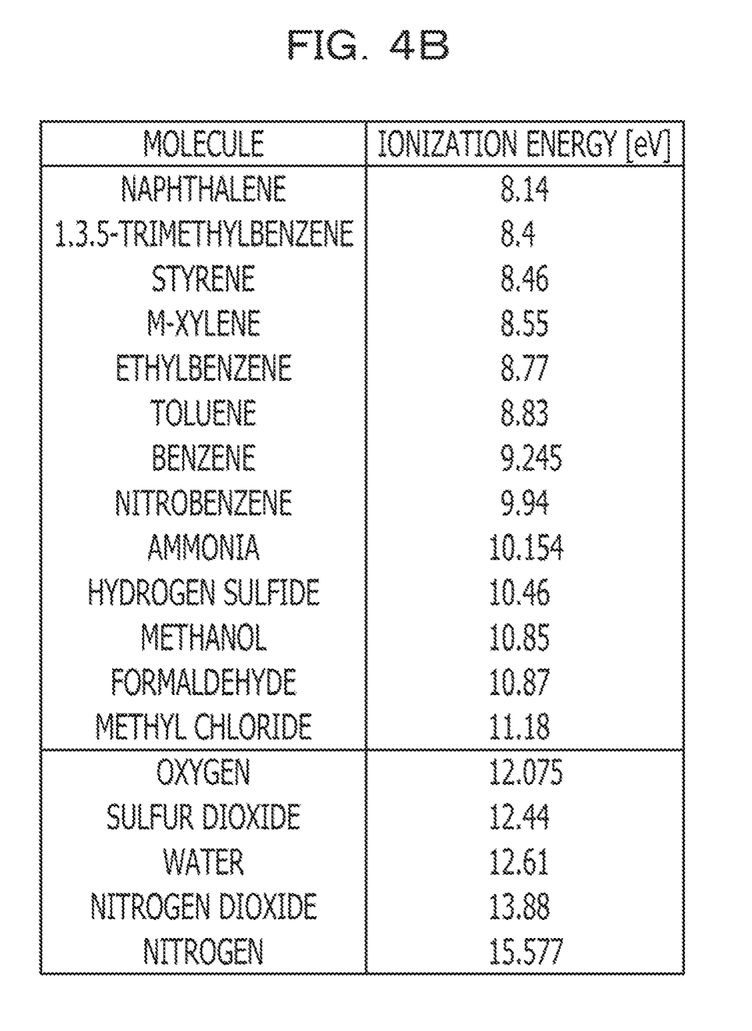
FIG. 4B is a table showing ionization energy of exemplary molecules.

FIG. 4B is a table showing ionization energy of various substances. For example, water molecules have an ionization energy of 12.61 eV, oxygen has an ionization energy of 12.08 eV, and nitrogen has an ionization energy of 15.58 eV. Therefore, these substances are not ionized by ultraviolet light from a deuterium discharge tube with a MgF2 window which emits only vacuum ultraviolet light with an energy of 10.78 eV or less. By not ionizing substances which are not required to be detected, the noise level can be decreased, and detection accuracy can be improved.

When one-photon ionization is performed using the detection device, all the substances that have an ionization energy lower than the photon energy can be ionized. It is difficult to identify which substances have the resulting mass, and it is difficult to refine the detection results. Furthermore, a short wavelength (high energy) ultraviolet light source, such as a deuterium discharge tube with a MgF2 window, is a unique light source and has a short life of use.

In general, a substance has a specific (atomic or molecular) energy state. The energy state has energy levels distributed in the electronic structure and a continuous band substantially equal to or higher than a vacuum level. Electrons are distributed in orbitals from lower to higher levels. The inner-shell orbitals filled with electrons are chemically inactive, and only electrons in the outer-shell orbital are usually taken into consideration. The electronic state having the lowest energy corresponds to the ground state. An energy level higher than the ground state is usually an empty state and is referred to as an excited energy level. If an electron in the ground state is excited, the electron can be excited to the excited energy level or a continuous band substantially equal to or higher than a vacuum level. The energy between atomic or molecular levels usually corresponds to photon energy in the ultraviolet light region.

The present inventors have studied two-photon ionization, instead of one-photon ionization, of a substance to be measured. That is, if an electron is excited by a first photon from a ground state to an excited state, and then excited by a second photon from the excited state to a continuous band substantially equal to or higher than a vacuum level, the electron becomes a free electron and flies outward, and thus ionization can occur. The energy level is specific to a substance, and the energy difference between the ground state and the excited state is also specific to a substance. By irradiation with ultraviolet light having specific energy corresponding to the substance-specific energy difference, a specific substance (atom or molecule) can be excited. If energy (photon) that is higher than the energy difference between the excited level and the vacuum level is applied to a substance in the excited state, ionization can be performed, and ions can be detected. That is, the detected substance can be identified. Since ionization from the ground state is performed by two-stage excitation, excitation energy in each stage is lowered, and the intention can be achieved using longer-wavelength light.

A substance detection device according to a first embodiment of the present invention will be described below.

Figure 1A:
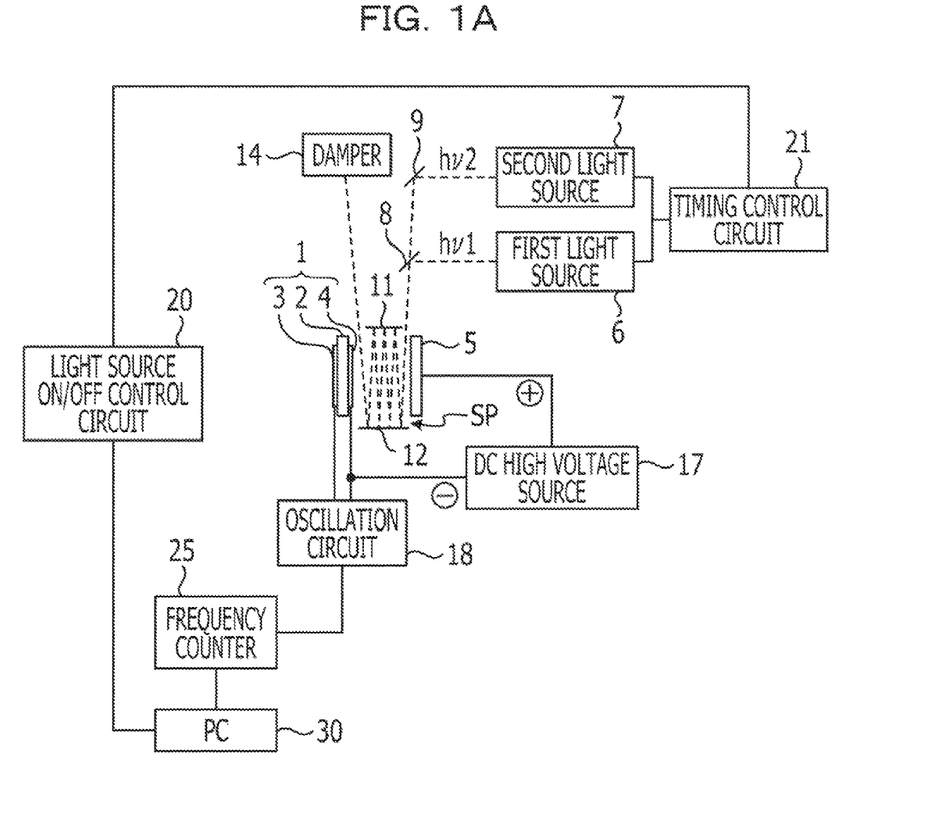
FIG. 1A is a block diagram of a substance detection device according to a first embodiment.

As illustrated in FIG. 1A, a quartz oscillator 1, which includes a quartz plate 2 and electrodes 3 and 4 provided on surfaces thereof, is exposed to an atmosphere containing a pollutant which is a detection target (i.e., target substance). A counter electrode 5 is disposed at a distance from the quartz oscillator 1 to form a detection space SP. First light from a first light source 6 is guided via a mirror 8 to the detection space SP, and is subjected to multiple reflection between facing reflectors 11 and 12 which are disposed substantially parallel to each other. Second light from a second light source 7 is guided via a mirror 9 to the detection space SP, and is subjected to multiple reflection between facing reflectors 11 and 12. By increasing the number of reflections by multiple reflection, the optical path length is extended so that the reaction between light and the atmosphere is enhanced. In addition, a damper 14 for absorbing light that has not been consumed may be provided.

As illustrated in FIG. 1A, in the case where optical paths of the first light and the second light overlap with each other, in order to transmit the second light, a dichroic mirror including a dielectric multilayer film or the like, a half mirror, or the like may be used as the mirror 8.

The first light source 6 and the second light source 7 are each composed of, for example, an optical parametric oscillator (OPO) pulsed laser using beta-barium borate (β-Ba2B2O4, BBO) crystals. Pulsed laser beams in which the oscillation wavelength is adjusted can be emitted. The pulse width may be several nanoseconds to several tens of nanoseconds. The energy density is low at the rising edge of pulse. The excited state of molecules has a short life. In order to perform irradiation with the second light in the state where as many molecules as possible are excited to the excited state, the second light is preferably delayed, for example, by about 1 nsec to 50 nsec, from the first light.

A light source on/off control circuit 20 and a timing control circuit 21 control the on/off of light emitted from the first light source 6 and second light source 7 and the timing thereof. The second pulsed light is emitted about 1 nsec to 50 nsec, for example, about 10 nsec, after the first pulsed light is emitted.

Figure 1B:
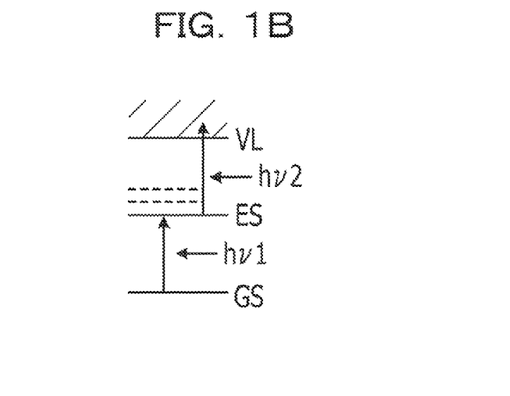
FIG. 1B is a diagram illustrating a mechanism of two-photon ionization.

As illustrated in FIG. 1B, energy hv1 of the first light excites the molecules of the target substance from the ground state GS to the selected excited state ES. Energy hv2 of the second light excites the molecules of the target substance from the excited state ES to the continuous band substantially equal to or higher than the vacuum level VL. Since the electrons in the continuous band become free electrons and are separated from the molecules, the remaining molecules become ions. It is required that the energy hv1 of the first light is substantially equal to the energy difference between the ground state GS and the excited state ES. By selecting the energy hv1 of the first light, the substance to be detected is selected.

A DC voltage source 17 is coupled between the electrode 4 and the counter electrode 5. It can also be considered that the DC voltage source 17 is coupled between the counter electrode 5 and the electrodes 3 and 4 of the quartz oscillator 1. The distance between the electrode 4 and the counter electrode 5 is, for example, about 2 cm, and the DC voltage is, for example, about 200 V. When a DC voltage is applied, a DC electric field directed from the counter electrode 5 toward the electrode 4 (quartz oscillator 1) is formed in the detection space SP. Cations generated in the detection space are accelerated by the electric field, reach the quartz oscillator 1, and adsorb to the quartz oscillator 1.

An oscillation circuit 18 is coupled between the electrodes 3 and 4 of the quartz oscillator to form an oscillation circuit. The oscillation frequency of the oscillation circuit 18 is detected by a frequency counter 25. When adsorption of the substance increases the mass of the quartz oscillator 1, the oscillation frequency changes. On the basis of the change in oscillation frequency, the mass (weight) of the adsorbed substance can be detected.

A central control unit 30 controls the light source on/off control circuit to control the on/off of the first light and the second light, and detects the change in frequency by phase lock detection. Description will now be made with reference to examples of specific substances to be detected.

Figure 2A:
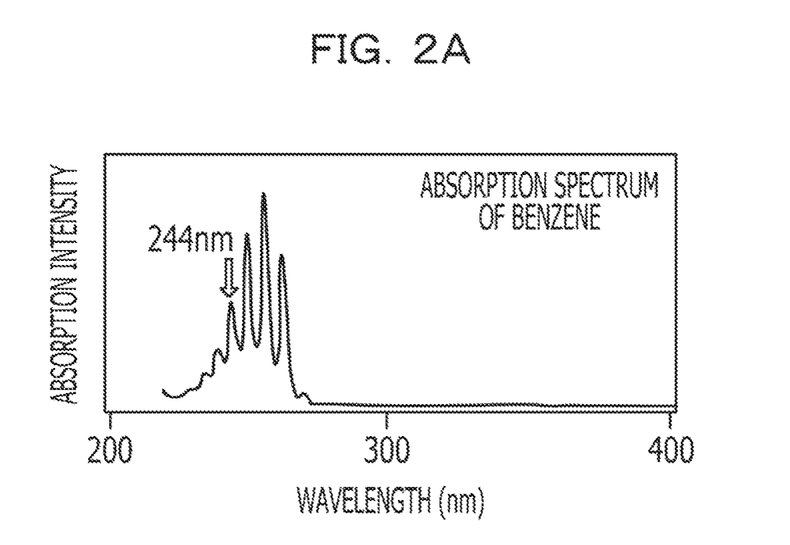
FIG. 2A is a graph illustrating an absorption spectrum of benzene.

FIG. 2A is a graph illustrating an absorption spectrum of benzene. The horizontal axis represents the wavelength, and the vertical axis represents the absorption intensity. The spectrum shows several absorption peaks in the ultraviolet wavelength region with a wavelength of 220 nm to 270 nm, and four absorption peaks are particularly strong. For example, the wavelength of the first light is matched to the absorption peak at 244 nm (5.08 eV). This corresponds to the transition from the ground state to the singlet minimum excited state of electrons. The ionization energy of benzene is 9.24 eV, and the energy from the excited state to the vacuum level is 4.16 eV (297 nm). The second light is light having a wavelength shorter than 297 nm.

Figure 2B:
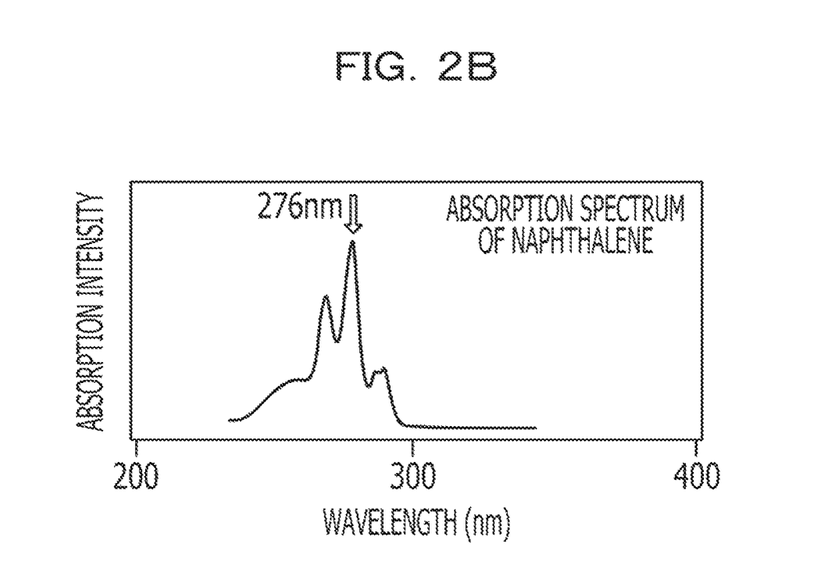
FIG. 2B is a graph illustrating an absorption spectrum of naphthalene.

FIG. 2B is a graph illustrating an absorption spectrum of naphthalene. The horizontal axis represents the wavelength, and the vertical axis represents the absorption intensity. The spectrum shows several absorption peaks in the ultraviolet wavelength region with a wavelength of about 250 nm to 290 nm, and two absorption peaks are particularly strong. For example, the wavelength of the first light is matched to the absorption peak at 276 nm (4.49 eV). This corresponds to the transition from the ground state to the singlet minimum excited state of electrons. The ionization energy of naphthalene is 8.14 eV, and the energy from the excited state to the vacuum level is 3.65 eV (339 nm). The second light is light having a wavelength shorter than 339 nm.

Any second light may be used as long as electrons can be excited from the excited state to energy substantially equal to or higher than the vacuum level. In general, as the wavelength becomes shorter, light in the vacuum ultraviolet region may become difficult to obtain (the intensity tends to be weakened), and as the transition energy decreases, the transition probability increases. Consequently, it is preferable to select a second light having energy that slightly exceeds the energy from the excited state to the vacuum level (a slightly shorter wavelength).

Figure 3:
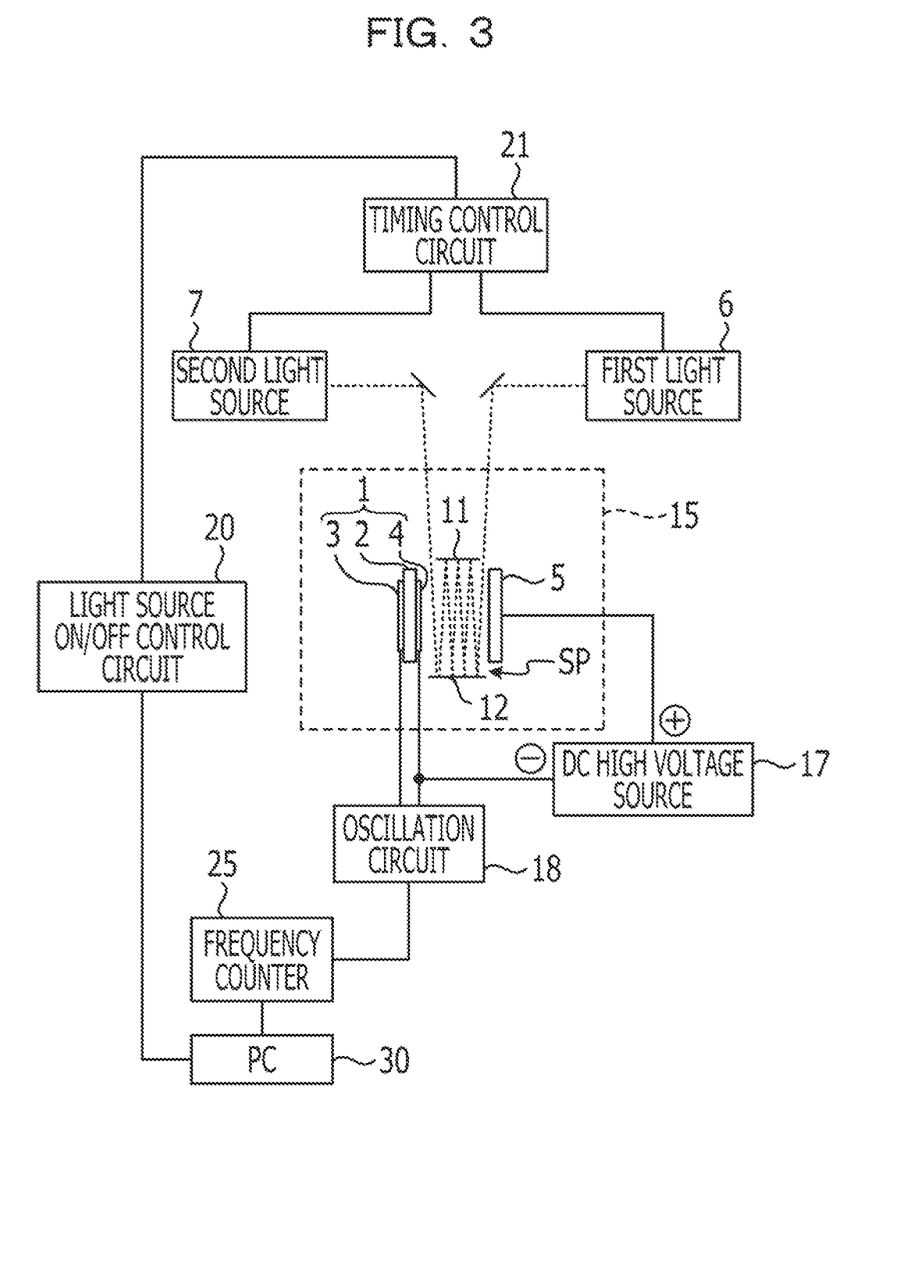
FIG. 3 is a block diagram of a substance detection device according to a second embodiment.

FIG. 3 is a block diagram of a substance detection device according to a second embodiment. Differences from the first embodiment will be mainly described. A first light source 6 and a second light source 7 emit light which enter from the opposite sides of multiple reflection mirrors 11 and 12. Mirrors 8 and 9 may be total reflection metal mirrors. Even if the optical path of the first light and the optical path of the second light in the detection space SP sandwiched between the multiple reflection mirrors 11 and 12 are entirely overlapped with each other, it may not be necessary to use a dichroic mirror or a half mirror. The detection space SP is surrounded by a metal mesh 15, which is coupled to a positive electric potential. Some sort of ions can be present in the atmosphere even in the state where irradiation with ultraviolet light may not be performed. Ions are repelled by the positive electric potential of the mesh and may not enter the detection space. The target substance that is not charged in the air is not affected by the positive electric potential of the mesh and can easily reach the detection target space.

Although the case of QCM using the quartz oscillator has been described, it is also possible to measure the mass of an adsorbed substance using a surface acoustic wave element.

Figure 5:
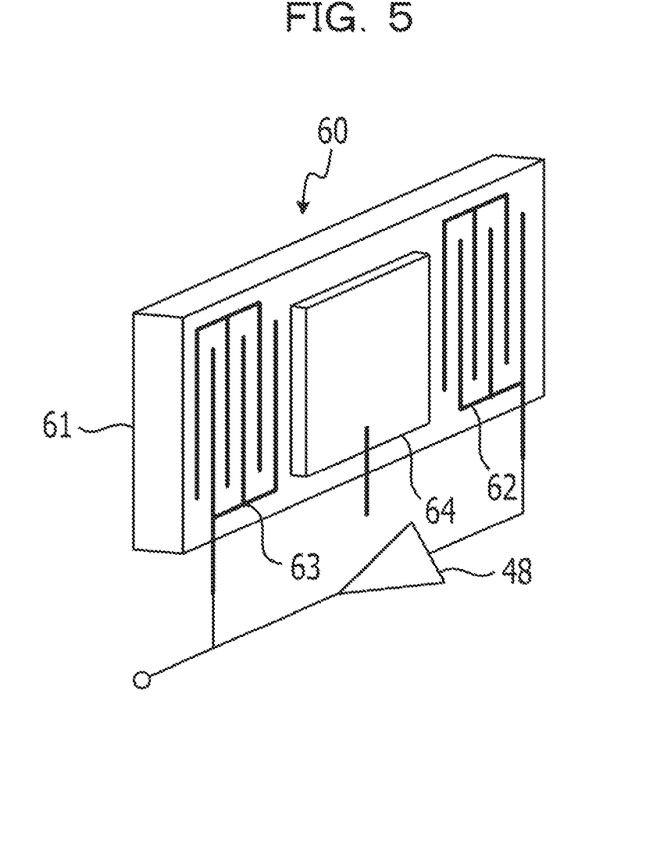
FIG. 5 is a perspective view schematically illustrating a structure of a surface acoustic wave element.

FIG. 5 is a perspective view schematically illustrating a structure of a surface acoustic wave element. A surface acoustic wave element 60 includes a LiTaO3 substrate 61 provided with an input electrode 62 and an output electrode 63, the ends of which are coupled to each other via an amplifier 48, and also provided with a sensor electrode, i.e., substance adsorption electrode 64, disposed between the electrodes. The surface acoustic wave element 60 may be used instead of the quartz oscillator 1 illustrated in FIG. 1A or FIG. 3, in which a counter electrode 5 may be placed so as to face the substance adsorption electrode 64, for example at a distance of 5 mm.

All examples and conditional language recited herein are intended for pedagogical purposes to aid the reader in understanding the invention and the concepts contributed by the inventor to furthering the art, and are to be construed as being without limitation to such specifically recited examples and conditions. Although the embodiments in accordance with aspects of the present invention have been described in detail, it should be understood that various changes, substitutions, and alterations could be made hereto without departing from the spirit and scope of the invention.

What is claimed is:
1. A detection method of detecting a target substance, the method comprising:
    exciting the target substance by irradiating an atmosphere of a detection space with light having a first wavelength that excites the target substance from a ground state to an excited state on the basis of the energy level structure of the target substance;

ionizing the target substance by irradiating the atmosphere of the detection space with light having a second wavelength that excites the target substance from the excited state to an energy state substantially equal to or higher than a vacuum level;

making the ionized target substance adsorb to a detector by electric field acceleration; and detecting the amount of adsorption of the target substance, wherein the light having the first wavelength and the light having the second wavelength are each pulsed light, and the irradiation of the pulsed light having the second wavelength is delayed from the irradiation of the pulsed light having the first wavelength.

2. The detection method according to claim 1, wherein the light having the first wavelength and the light having the second wavelength are guided in the atmosphere through the same path.

3. The detection method according to claim 1, wherein the amount of adsorption is detected by synchronizing the on/off of the light having the first wavelength and the light having the second wavelength.

4. A detection device comprising:
   a detector configured to detect the amount of adsorption of a target substance;
   a counter electrode configured to face the detector with a detection space therebetween;
   a first light source configured to irradiate the detection space with light having a first wavelength having an energy substantially equal to a difference between a ground energy level and an excited energy level of the target substance;
   a second light source configured to irradiate the detection space with light having a second wavelength having an energy substantially equal to or higher than a difference between the excited energy level and a vacuum level of the target substance;
   an acceleration power source configured to form an acceleration electric field between the counter electrode and the detector;
   a detection circuit configured to supply a detection signal to the detector; and
   a control circuit configured to control the emission timing of the first light source and the second light source.

5. The substance detection device according to claim 4, further comprising:
   a first reflection element configured to guide the light from the first light source to a light path; and
   a second reflection element configured to guide the light from the second light source to the light path.

6. The substance detection device according to claim 4, wherein the detector is a quartz oscillator or a surface acoustic wave element.

7. The substance detection device according to claim 4, wherein the first light source and the second light source are each an optical parametric oscillator pulsed laser.

8. The substance detection device according to claim 4, wherein the detection circuit detects a frequency generated by the detector to detect the amount of adsorption of a target substance.

9. The substance detection device according to claim 4, wherein the detection circuit includes:
   an oscillator configured to supply the detection signal to the detector; and
   a frequency counter configured to detect a frequency generated by the detector.

* * * * *